US 6,399,310 B1
Jun. 4, 2002

(54) METHODS FOR IMPROVING THE THERAPEUTIC RESPONSE OF HUMANS HAVING MAJOR DEPRESSION AND CARRYING THE GENE FOR APOLIPOPROTEIN E4

(75) Inventors: Greer M. Murphy, Jr., Stanford; Alan F. Schatzberg, Los Altos, both of CA (US)

(73) Assignee: Akzo Nobel N.V. (NL)

( * ) Notice: Subject to any disclaimer, the term of this patent is extended or adjusted under 35 U.S.C. 154(b) by 0 days.

(21) Appl. No.: 09/780,512

(22) Filed: Feb. 12, 2001

(51) Int. Cl.$^7$ ................................................ C12Q 1/68
(52) U.S. Cl. ............................ 435/6; 435/7.1; 435/536
(58) Field of Search ...................... 435/6, 7.1; 436/536; 530/412

(56) References Cited

U.S. PATENT DOCUMENTS

| | | | |
|---|---|---|---|
| 4,062,848 A | 12/1977 | van der Burg | 260/268 |
| 4,515,792 A | 5/1985 | Watthey | 514/214 |
| 5,082,864 A | 1/1992 | Van den Oetelaar et al. | 424/466 |
| 5,178,878 A | 1/1993 | Wehling et al. | 424/66 |
| 5,508,167 A | 4/1996 | Roses et al. | 435/6 |
| 5,767,248 A | 6/1998 | Roses et al. | 530/388.25 |
| 5,935,781 A | 8/1999 | Poirier | 435/6 |
| 5,977,099 A | 11/1999 | Nickolson | 514/214 |
| 5,985,936 A | 11/1999 | Novak | 514/724 |
| 6,022,683 A | 2/2000 | Poirier | 435/4 |
| 6,027,896 A | 2/2000 | Roses et al. | 435/6 |
| 6,027,899 A | 2/2000 | Lehmann et al. | 435/6 |
| 6,063,573 A | 5/2000 | Kayyem | 435/6 |
| 6,096,742 A | 8/2000 | Crocker et al. | 514/214 |
| 6,114,324 A | 9/2000 | Skrabanja et al. | 514/214 |
| 6,117,855 A | 9/2000 | Carlson et al. | 514/90 |
| 6,150,353 A | 11/2000 | Broekkamp et al. | 514/214.02 |

OTHER PUBLICATIONS

Holmes et al. Biological Psychiatry (Feb. 1, 1998) 43/3: 159–164.*
Aksari, P. et al., Fortschr. Neurol. Psychiat. 64:425–432, 1996.
Andreasen, N. et al., Neurology 53: 1488–1494, 1999.
Bellivier, F. et al., Neuroscience Letters 233: 45–48, 1997.
Benkert, O. et al., J. Clin. Psychiatry 61:656–663, 2000.
Buttini, M. et al., Neurosci. 97:207–210, 2000.
Cantillon, M. et al., Biol. Psychiatry 41:246–248, 1997.
Crawford, J.G., Medical Hypotheses 50:25–36, 1998.
Dal Forno, G. et al., Arch. Neurol., 53:345–350, 1996.
de Boer, T., Int. Clin. Psychopharmacol. 10 Suppl. 4:19–23, 1995.
de Boer, T., J. Clin. Psychiatry 57(suppl4):19–25, 1996.
DeKosky, S.T. et al., Ann. N.Y. Acad. Sci. 802:27–34, 1996.
Diagnostic and Statistical Manual of Mental Disorders, 4$^{th}$ Ed.:375–376, 2000.

Farrer, L.A. et al., JAMA 278:2349–1356,1997.
Folstein, M.F. et al., J. Psychiatr. Res. 12:189–198, 1975.
Forsell, Y. et al., Biol. Psychiatry 42:898–903, 1997.
Guy, W., ECDEU Assessment Manual for Psychopharmacology, DHEW; Publ. No. (ADM) 76–338, rev. 1976, pp. 218–222.
Hamilton, M. et al., Br. J. Soc. Clin. Psychol. 6:278–296.
Heidrich, A. et al., Biol. Psychiatry 41:912–914, 1997.
Hirono, N. et al., J. Neuropsychiatry Clin. Neurosci. 11:66–70, 1999.
Hixson, J.E. et al., J. Lipid Res. 31:545–548, 1990.
Juva, K. et al., Neurology 54:412–415, 2000.
Kasper, S. et al., Drug Safety 17:251–264, 1997.
Katzel, L.I. et al., Am. J. Cardiol. 81:261–265, 1998.
Katzman, R. et al., Brain Cogn. 28:259–265, 1995.
Krishnan, K. et al., Biol. Psychiatry 40:69–71, 1996.
Krishnan, K. et al., Neurology 44:2420–2421, 1994.
Lavretsky, H. et al., Am. J. Geriatric Psychiatry 8:3, 257–261, 2000.
Leinonen, E. et al., Int. Clin. Psychopharmacol. 14:329–337, 1999.
Lendon, C.L. et al., Eur. J. Neurosci., 12:2235–2242, 2000.
Levy, M. et al., Biol. Psychiatry 45:422–425, 1999.
Mahley R. W. et al., 1983, Biochem. Biophys. Acta. 737:197–222, 1983.
Mauricio, M. et al., Am J Geriatric Psychiatry 8:196–200; 2000.
Montgomery, S. et al., Int. Clin. Psychopharmacol. 12:63–73, 1998.
Mulsant, B.H. et al., J. Clin. Psychiatr. 60:16–20, 1999.
Murphy, G. et al., Am. J. Psychiatry 154:603–608, 1997.
Nacmias, B. et al., Neuroscience Letters 244:85–88, 1998.
O'Hara, E. et al., J. Am. Geriatr. Soc. 46:1493–1498, 1998.
Ohara, K. et al., Psychiatry Res. 88:221–226, 1999.
Papassotiropoulos, A. et al., Dement. Geriatr. Cogn. Disord. 10:258–261, 1999.
Papassotiropoulos, A. et al., Neuroscience Letters, 262: 171–174, 1999.

(List continued on next page.)

Primary Examiner—Lisa B. Arthur
(74) Attorney, Agent, or Firm—Finnegan, Henderson, Farabow, Garrett & Dunner, LLP

(57) ABSTRACT

This invention relates to methods for improving the therapeutic response of human patients with major depression by determining the apolipoprotein E genotype of a human patient and administering mirtazapine, in an amount effective to treat major depression, to those patients who are found to carry the gene for apolipoprotein E4. Also disclosed are methods for improving the therapeutic response of a human patient with major depression comprising administering mirtazapine, in an amount effective to treat major depression, to a human patient who is a carrier of the gene for apolipoprotein E4.

18 Claims, No Drawings

OTHER PUBLICATIONS

Pickar, D. et al., Lancet 350:930–931, 1997.
Poirier, J. et al., Mol. Brain. Res., 9:191–195, 1991.
Poirier, J. et al., Mol. Brain. Res., 11:97–106, 1991.
Poirier, J. et al., Neuroscience, 55:81–90, 1993.
Rigaud, A–S et al., Eur. J. Neurol., 7:255–258, 2000.
Roheim, P. S. et al., Proc. Natl. Acad. Sci., 76:4646–4649, 1979.
Sawa, A. et al., Mol. Psychiatry 2:341–342, 1997.
Schmand, B. et al., Soc. Psychiatry Psychiatr. Epidermiol. 33:21–26, 1998.
Stahl, S. et al., Acta Psychiatr. Scand. Suppl. 391:22–30, 1997.
Steffens, D.C. et al., Biol. Psychiatry 41:851–856, 1997.
Van Rensburg, S.J. et al., Ann. N.Y. Acad. Sci. 903: 200–203, 2000.
Walters, G. et al., J. Clin. Psychiatr. 60:21–25, 1999.
Wheatley, D.P. et al., J. Clin. Psychiatr. 59:306–312, 1998.
Yaffe, K. et al., Arch. Neurol. 54:1110–1114, 1997.
Yesavage, J.A. et al., J. Psychiatr. Res. 17:37–49, 1983.
Remeron® (mirtazapine) Tablets—Package Insert (Mar. 1999).
Schatzberg, A.F. et al., Amer. Coll. of Neuropsychopharmacol., 39th Annual Mtg., Scientific Abstracts/Poster Session I, p. 97 (Dec. 10–14, 2000).
Murphy, G.M. et al., Amer. Coll. of Neuropsychopharmacol., $39^{th}$ Annual Mtg., Scientific Abstracts/Poster Session II, p. 235 (Dec. 10–14, 2000).

* cited by examiner

METHODS FOR IMPROVING THE THERAPEUTIC RESPONSE OF HUMANS HAVING MAJOR DEPRESSION AND CARRYING THE GENE FOR APOLIPOPROTEIN E4

FIELD OF THE INVENTION

The present invention relates to methods for improving the therapeutic response of human patients with major depression, particularly those carrying the gene for apolipoprotein E4.

BACKGROUND OF THE INVENTION

Psychiatric diseases generally provide a unique set of complications for clinicians, patients, and care givers. Major depression, for instance, is a major health problem and poses a tremendous financial burden on society due to lost self-support of individuals suffering from depression. Such individuals are often simply unable to function in everyday life situations, in part because of feelings of extreme hopelessness and worthlessness. There is also a serious risk of suicide among such individuals. The various forms of depression are defined and are separately diagnosed according to criteria given in handbooks for psychiatry, for example in the Diagnostic and Statistical Manual of Mental Disorders 4th edition (DSM-IV) published by the American Psychiatric Association, Washington, D.C. (1994). The diagnostic criteria for major depression are well known to those skilled in the art, and comprise the criteria set forth, for example, at DSM-IV 296.2 and 296.3. Major depression, defined in more detail below, is also known as major depressive disorder and is estimated to affect between 5 to 10% of the human population.

Although treatments for different types of depression do exist, there is a continuous search for new methods of treatment of depression because existing methods still have disadvantages, such as the side effects of drugs, the long duration of treatments, and, more importantly, the partial efficacy (or inefficacy) of treatments. For example, there is wide variation in the response of patients with major depression to antidepressant pharmacotherapy. Some of this variation may be due to genetic differences among patients. Regardless, the result is that about 30% of patients with major depression who are treated with existing antidepressant drugs do not improve.

Among the various drugs available for therapy of depression, there are groups of drugs with totally different mechanisms of action. Such mechanisms include, for example, the blockage of reuptake of serotonin; the blockage of reuptake of noradrenaline; or the blockage of presynaptic receptors on noradrenergic or serotonergic nerve terminals. Such different mechanisms of action make it possible to make conscious choices regarding treatments for depression based on different biochemical mechanisms. However, it has not been known which characteristics of a patient predict a better response to one particular kind of drug over another, so treatment choices have been complicated by the fact that it often takes a significant period of treatment to determine whether or not a drug is having a therapeutic effect or is merely slower in having its therapeutic effect.

Accordingly, treatment with the most effective drug(s) is often delayed while the disease continues to disrupt daily functioning of the patient. Even a patient who may ultimately improve after weeks or months of treatment with one drug may have improved much faster with another drug if only it had been tried sooner. Thus the failure to treat the disease in the most effective manner results in lessened quality of life for the patient not only in the immediate time frame but also in the foreseeable future.

Currently, the expanding field of pharmacogenetics would like to identify DNA markers for differential medication response, thereby using these markers to individualize patient treatment in order to maximize therapeutic response and minimize side effects. Thus, a method which would allow one to predict which patients will respond to specific therapeutics and dosages would provide physical and psychological benefits. Specifically, the efficacy of antidepressant treatment would be greatly improved if there were better methods available to identify the patients which would respond the fastest and with the best therapeutical benefit to a particular kind of treatment.

One characteristic that has been studied extensively with respect to Alzheimer's Disease (AD) and possible treatments thereof is the gene for apolipoprotein E (apoE). The apoE gene on chromosome 19 has three common alleles ($\epsilon 2$, $\epsilon 3$, and $\epsilon 4$), which encode three major apoE isoforms (E2, E3, and E4). The three alleles correspond to six genotypes, i.e., $\epsilon 2/\epsilon 2$, $\epsilon 2/\epsilon 3$, $\epsilon 2/\epsilon 4$, $\epsilon 3/\epsilon 3$, $\epsilon 3/\epsilon 4$, and $\epsilon 4/\epsilon 4$. In typical populations, for example, $\epsilon 3$ is the most common allele, occurring on more than 75% of chromosomes. The average frequency of $\epsilon 2$ is 8% and the average frequency of $\epsilon 4$ is 15%. See, e.g., Farrer, L. A. et al., JAMA 278:1349–1356, 1997.

ApoE functions as a ligand in the process of receptor mediated internalization of lipid-rich lipoproteins, and it is probably also involved in reverse lipid transport. See, e.g., Mahley, R. W. et al., Biochem: Biophys. Acta. 737:197–222 (1983). In the central nervous system, apoE plays a central role in the mobilization and redistribution of cholesterol and phospholipid during membrane remodeling associated with synaptic plasticity. See, e.g., Poirier, J. et al., Mol. Brain. Res., 9:191–195 (1991); Poirier, J. et al., Mol. Brain. Res., 11:97–106 (1991); Poirier, J. et al., Neuroscience, 55:81–90 (1993).

In view of the studies with Alzheimer's disease, the apoE $\epsilon 4$ allele has been found to be an established genetic risk factor for Alzheimer's disease. See, e.g., Hirono, N. et al., J. Neuropsych. Clin. Neurosci. 11:66–70 (1999). In contrast, the art provides no evidence that the apoE $\epsilon 4$ allele is a risk factor for major depression. See e.g., Mauricio, M. et al., Am. J. Geriatr. Psychiatr. 8:196–200 (2000); Forsell, Y. et al., Biol. Psychiatry 42: 898–903 (1997); Heidrich, A. et al., Biol. Psychiatry 41:912–914 (1997); Papassotiropoulos, A. et al., Dement. Geriatr. Cogn. Disord. 10:258–261 (1999); and Schmand, B. et al., Soc. Psychiatry Psychiatr. Epidemiol. 33: 21–26 (1998).

With respect to Alzheimer's, although it is not determinative of the disease, it has been found that human patients carrying at least one apoE $\epsilon 4$ allele have a much greater chance of developing the disease. See, e.g., Levy, M. et al., Biol. Psychiatry 45:422–425 (1999). In addition, the apoE $\epsilon 4$ allele has been associated with cognitive deficits in nondemented elderly in a number of studies. See, e.g., O'Hara, R. et al., J. Am. Geriatr. Soc. 46:1493–1498, (1998). There are several reasons why nondemented elderly patients who suffer from mild cognitive impairment associated with carrying the apoE $\epsilon 4$ allele may have been poorly responsive to certain antidepressant medication treatments. First, nondemented depressed subjects carrying the apoE $\epsilon 4$ allele may have mild brain dysfunction rendering them unresponsive to the therapeutic neurochemical changes induced by antidepressant agents. Second, recovery from depression is currently thought to depend in part on a restructuring of cognition and behavior that maintains the depressed mood. Mild cognitive impairment in apoE ε4 allele carriers may have made it difficult for these individuals to effect the cognitive changes necessary for recovery from depression. Finally, certain types of anti-depressant drugs, e.g., paroxetine, may negatively affect cognition, and subjects with the apoE ε4 allele may be more vulnerable to such effects than subjects without the allele.

Thus, one would have expected carriers of the apoE ε4 allele to be poor candidates for treatment of major depression.

SUMMARY OF THE INVENTION

Surprisingly, however, the inventors have found, as a result of clinical trials described herein, that for at least one antidepressant drug, mirtazapine, there are clear improvements in therapeutic response among patients with at least one apoE ε4 allele as opposed to those without an apoE ε4 allele. Specifically, mirtazapine has been found to be particularly effective as an antidepressant for apoE ε4 carriers. This biochemical trait difference in depressed patients can be used to predict a faster and more effective therapeutic response to mirtazapine. In other words, the present inventive method may be used to identify depressed patients who are most likely to show a very good response to mirtazapine.

Mirtazapine is an antidepressant drug, known as a NaSSA (a Noradrenergic and Specific Serotonergic Antidepressant). Mirtazapine has been marketed for the treatment of major depression by Organon Inc. under the tradename REMERON®. Mirtazapine is disclosed in U.S. Pat. No. 4,062,848, the disclosure of which is hereby incorporated by reference. Mirtazapine belongs to the piperazino-azepine group of compounds and is designated 1,2,3,4,10,14b-hexahydro-2-methylpyrazino[2,1-a]pyrido[2,3-c]benzazepine. Mirtazapine increases both noradronergic and serotonergic neurotransmission by blocking both central $\alpha_2$-adrenergic autoreceptors and $\alpha_2$-adrenergic heteroreceptors and selectively blocking the 5-HT$_2$ and 5-HT$_3$ receptors. See, e.g., de Boer, T., J. Clin. Psychiatry 57 suppl 4:19–25 (1996).

Thus, the present invention relates to methods for improving the therapeutic response of a human patient with major depression by administering mirtazapine, in an amount effective to treat major depression, to a human patient carrying the gene for apolipoprotein ε4. The invention also relates to methods for improving the therapeutic response of human patients with major depression by determining the apolipoprotein E genotype of a human patient and then administering mirtazapine, in an amount effective to treat major depression, to those human patients who are found to carry the gene for apolipoprotein ε4.

DETAILED DESCRIPTION OF THE PREFERRED EMBODIMENTS

For purposes of the present invention, the following terms are defined:

"Alzheimer's Disease (AD)" means a pathology characterized by an early and extensive loss of entorhinal cortex neurons, and by neuritic plaques and neurofibrillary tangles. AD patients may be identified by progressive and degenerative effects on the brain which cannot be attributed to causes other than AD.

"Determining the apolipoprotein (apoE) genotype" means screening patients to determine the type and number of apoE alleles present in the patient. Such screening may be carried out by nucleic acid sequencing of DNA. For example, the screening may be accomplished by restriction isotyping methods, which include the general steps of polymerase chain reaction amplification, restriction digestion, and gel electrophoresis. Screening may also be carried out by other types of nucleic acid sequencing, e.g., by hybridization or oligotyping. Alternatively, the screening may involve examination of which apolipoprotein isoforms are present in the patient's plasma, or "phenotyping".

"Gene for apolipoprotein E (apoE gene)" means the gene which encodes for the three major isoforms (apoE2, apoE3, and apoE4) of apolipoprotein E. The apoE gene on chromosome 19 has three common alleles (ε2, ε3, and ε4) which correspond to the three isoforms apoE2, apoE3, and apoE4.

"Gene for apolipoprotein E4 (apoE4 gene)", means the gene which encodes for apoE4 via one of three genotypes: ε2/4, ε3/ε4, and ε4/ε4. This term is used interchangeably herein with the term "apoE ε4 allele", i.e., the specific allele that encodes for apoE4. The DNA and amino acid sequences of the apoE4 gene and of apoE4 itself are known and are available, e.g., at GenBank Accession No. M10065.

"Improved therapeutic response" or "improving the therapeutic response" means a faster onset of antidepressant action of a particular drug treatment, and a better treatment result, e.g., in terms of reducing or eliminating the symptoms of depression.

"Major depression" or "major depressive disorder" is defined by the occurrene of at least one major depressive episode. Such an episode implies a prominent and relatively persistent (nearly every day for at least 2 weeks) depressed or dysphoric mood that usually interferes with daily functioning, and includes at least five of the following nine symptoms: depressed mood, loss of interest in usual activities, significant change in weight and/or appetite, insomnia or hypersomnia, psychomotor agitation or retardation, increased fatigue, feelings of guilt or worthlessness, slowed thinking or impaired concentration, a suicide attempt or suicidal ideation.

According to the present invention, the therapeutic response of a human patient with major depression is improved by administering mirtazapine, in an amount effective to treat major depression, to human patients carrying the gene for apoE4. In another embodiment of the invention, the therapeutic response of a human patient with major depression is improved by determining the apolipoprotein E genotype of a human patient and then administering mirtazapine, in an amount effective to treat major depression, to those patients who are found to carry the gene for apolipoprotein E4. As described above, the determination of apoE genotype is generally carried out either by phenotyping, e.g., analyzing apolipoprotein particles present in the patient's plasma, or by nucleic acid sequencing of DNA, e.g., a polymerase chain reaction approach, such as restriction isotyping. ApoE and the genetic sequences of the various genotypes of the apoE gene, including those for apoE4, are discussed, e.g., in Mahley, R. W. et al., Biochem. Biophys. Acta. 737:197–222 (1983) and in Hixson et al., J. Lipid Res. 31:545–548 (1990).

The amount of mirtazapine effective to treat major depression will, of course, vary and is ultimately at the discretion of the medical practitioner. The factors to be considered include the route of administration and nature of the formulation, the body weight, age, and general state of health, and severity of the depression. Unless otherwise stated, all weights of active ingredients referred to herein are calculated in terms of the active drug per se. In general, a suitable dose of mirtazapine for administration to a human will be in the range of 5 to 100 mg per day. In one embodiment, the suitable dosage range for administration of mirtazapine to a human may be 15 to 45 mg per day, The desired dose may be presented as two, three, four, five, or more sub-doses administered at appropriate intervals throughout the day. These sub-doses may be administered in unit dosage forms, for example, containing 7.5 mg, 15 mg, or 30 mg, or any unit dosage useful to allow multiple dosing in a single day.

Unless otherwise indicated, all numbers expressing quantities, reaction conditions, and so forth used herein are to be understood as being modified in all instances by the term "about." Accordingly, unless indicated to the contrary, the numerical parameters set forth in the specification herein and in the attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

Pharmaceutical formulations according to the present invention comprise mirtazapine together with at least one pharmaceutically acceptable carrier and optionally at least one other therapeutic agent. "Acceptable" means compatible with the other ingredients of the formulation and not deleterious to the recipient thereof. "Compatible" may be defined as "capable of forming a chemically or biochemically stable system." The formulations may also include, for example, excipients, fillers, binders, diluents, disintegrants, lubricants, colorants, flavoring agents, and wetting agents. Formulations include those suitable for oral, rectal, nasal, topical (including transdermal, buccal, mucosal, and sublingual), vaginal, or parenteral (including subcutaneous, intramuscular, intravenous, and intradermal) administration. The formulations may be prepared by any methods well known in the art of pharmacy, for example, using methods such as those described in Gennaro et al., Remington's Pharmaceutical Sciences (18th ed., Mack Publishing Company, 1990, see especially Part 8: Pharmaceutical Preparations and their Manufacture).

The forms for administration of mirtazapine may also vary greatly. Formulations suitable for oral administration may be presented as discrete units such as pills, tablets, or capsules, each containing a predetermined amount of active ingredient; as a powder or granules; as a solution or suspension. The active ingredient may also be present as a bolus or paste, or may be contained within liposomes. Formulations for rectal administration may be presented as a suppository or enema. For parenteral administration, suitable formulations include aqueous and nonaqueous sterile injection. The formulations may be presented in unit-dose or multi-dose containers, for example, sealed vials and ampoules, and may be stored in a freeze-dried (lyophilized) condition requiring only the addition of the sterile liquid carrier, for example water, prior to use. Formulations suitable for administration by nasal inhalation include fine dusts or mists which may be generated by means of metered dose pressurized aerosols, nebulizers or insufflators.

Mirtazapine may be prepared using the methods described in U.S. Pat. No. 4,062,848, the disclosure of which has been incorporated by reference above. A suitable pharmaceutical formulation for use in the present invention is REMERON® brand mirtazapine tablets. REMERON® is supplied for oral administration as scored, film-coated tablets containing either 15 or 30 mg of mirtazapine and unscored, film-coated tablets containing 45 mg of mirtazapine. Each tablet also contains corn starch, hydroxypropyl cellulose, magnesium stearate, colloidal silicon dioxide, lactose, and other inactive ingredients. Formulating suitable mirtazapine-containing tablets is thus well known to those skilled in the art.

In another embodiment, mirtazapine may be formulated in the form of a solid pharmaceutical dosage form adapted for oral administration, e.g., as taught in U.S. Pat. No. 5,178,878. As explained therein, such a dosage form includes a mixture incorporating at least one water and/or saliva activated effervescent disintegration agent and also microparticles which contain, inter alia, the pharmaceutical ingredient, in this case mirtazapine. This mixture may be used in the form of a tablet which substantially and completely disintegrates upon exposure to water and/or saliva, so that when the tablet is taken orally, the effervescent disintegration agent aids in rapid dissolution of the tablet and permits release of the microparticles, and swallowing of the microparticles, before the pharmaceutical ingredient is even release therefrom.

The invention is further illustrated, but not intended to be limited by, the following example:

EXAMPLE

A multi-center, randomized, double-blind, 8-week comparison of paroxetine and mirtazapine was performed for 246 nondemented, cognitively intact patients 65 years of age and older with major depression. All patients were genotyped at the apoE locus as discussed further below.

Drugs Used in the Study

The antidepressant paroxetine is a selective serotonin reuptake inhibitor (SSRI) that increases the availability of serotonin at synapses between neurons arising in the brainstem raphe nuclei and their target neurons in a variety of brain regions. This results in binding of serotonin with a variety of postsynaptic receptors. Paroxetine has been shown to be efficacious in the treatment of major depression including depression in geriatric patients (Mulsant, B. H. et al., J. Clin. Psychiatry 60:16–20, 1999; Walters, G. et al., J. Clin. Psychiatry 60:21–25, 1999).

Mirtazapine, also an antidepressant, induces the release of norepinephrine as well as serotonin in the brain (de Boer, T., Int. Clin. Psychopharmacol. 10 Suppl. 4:19–23, 1995). Mirtazapine also blocks $5HT_2$ and $5HT_3$ postsynaptic receptors at serotonergic synapses, leaving $5HT_1$ receptors free to interact directly with serotonin released into the synapse. As discussed above, mirtazapine has been shown to be efficacious in the treatment of major depression.

Dosages

After an initial evaluation period, the mirtazapine patients started with a 15 mg dose per day. After two weeks of treatment (Day 14), patients' dosages were raised to 30 mg per day. After four weeks of treatment (Day 28), subjects who did not rate "Much Improved" or "Very Much Improved" on the Clinical Global Impression (CGI) Scale (see below) were raised to 45 mg per day provided they were able to tolerate the previous dose. Subjects who rate "Much Improved" or "Very Much Improved" on the CGI Scale I continued on the same dose they were receiving during the previous week. After six weeks of treatment (Day 42), the dose for subjects who did not rate "Much Improved" or "Very Much Improved" on the CGI Scale (see below) was raised to 45 mg per day provided they were able to tolerate the previous dose.

For paroxetine, the dosing system was the same, except that the starting dosage was 20 mg per day, raised to 30 mg per day, and to a maximum of 40 mg per day.

Methods of Evaluation

Various methods of evaluation of the patients' depressed state included:

EFFICACY:

Hamilton Depression Rating Scale (HDRS; 17 and 21 item versions of a structured interview) (Hamilton, M., J. Neurol. Neurosurg. Psychiatr. 23:56–62, 1960; Hamilton, M., Br. J. Soc. Clin. Psychol. 6:278–296, 1967). The primary efficacy parameter is the number of HDRS-17 50% responders, defined as subjects who had a decrease on a post-baseline assessment of at least 50% as compared to baseline. HDRS-17 means that the first 17 items of the HDRS-21 interview were completed, thus an HDRS-21 50% responder would be a subject who completed all 21 items of the interview and had a decrease on a post-baseline assessment of at least 50% as compared to baseline. In other words, a lower rating in the HDRS scale signifies less depression. In contrast, HDRS remitters, which are those patients showing the least depression, are defined as subjects who have an HDRS-17 score of less than 7 at a post-baseline visit.

Geriatric Depression Scale (GDS) (Yesavage, J. A. et al., J. Psychiatr. Res. 17:37–49, 1983), a self-rating scale developed specifically for rating depression in the elderly. In the GDS, a lower rating signifies less depression. GDS 50% responders are defined as subjects with a decrease on a post-baseline assessment of at least 50% as compared to baseline.

Clinical Global Impression Scale (CGI) (Guy, W., ECDEU Assessment Manual for Psychopharmacology, DHEW Publication No. (ADM) 76–338, rev. 1976). The CGI scale is a global 7-point rating of the severity of the illness taking into account the preceding week (CGI-Severity) and a global 7-point rating of the clinical status of the subject since baseline (CGI-Change). A responder is defined as being "Much Improved" or "Very Much Improved" —having a CGI score of at least 2 according to CGI-Change. Thus, a higher CGI-Severity score corresponds to more severe depression whereas a higher CGI-Change score corresponds to lessened depression, or an improvement in alleviating the symptoms of depression.

COGNITION:

Mini Mental State Examination (MMSE) (Folstein, M. F. et al., J. Psychiatr. Res. 12:189–198, 1975). This test represents a brief standardized method to grade cognitive mental status. The test assesses orientation, attention, immediate and short-term recall, language, and the ability to follow verbal and written commands. The lower the score, the lower the cognitive mental status.

Genetic Analysis

To screen patients for the gene, genomic DNA was extracted from EDTA-treated whole blood using the Puregene DNA extraction kit (available from Gentra Systems). ApoE genotypes were determined using restriction isotyping (restriction enzyme isoform genotyping) according to the protocol of Hixson and Vernier (J. Lipid Res. 31:545–548, 1990), as set forth in Murphy, G. E. et al., Am. J. Psychiatr. 154:603–608, 1997. Genotypes were determined by two observers blind as to the clinical or neuropathological diagnosis.

Statistical Analysis

All statistical analyses were performed using the SAS software package (available from SAS Institute). For clinical measures of depression (HDRS-21, HDRS-17, GDS, and CGI), analyses of covariance were performed with baseline values as the covariate, and apoE genotype ($\epsilon 4$ allele carrier vs. non-carrier) and medication (mirtazapine, paroxetine) as the predictors. For remitter and responder analyses of clinical measures of depression, Cochran-Mantel-Haenszel statistics were used. For comparison of medication and genotype groups on baseline demographic measures, two-way analyses of variance were used.

Results

Of the 246 patients tested, 122 were treated with paroxetine and 124 treated with mirtazapine. Among the mirtazapine treated patients, 31 (25.0%) carried an $\epsilon 4$ allele, whereas among the paroxetine treated subjects, 30 (24.6%) were $\epsilon 4$ carriers. The mean ages for $\epsilon 4$ carriers and non-$\epsilon 4$ carriers were not significantly different among paroxetine and mirtazapine treated subjects. There were no significant differences in the numbers of males and females carrying $\epsilon 4$ alleles in either the paroxetine or the mirtazapine treatment groups. There were no differences in final daily dosage achieved, dosing compliance, or plasma drug concentrations between $\epsilon 4$ carriers and non-$\epsilon 4$ carriers for either mirtazapine or paroxetine. There were no significant differences between $\epsilon 4$ carriers and noncarriers in the number of patients who discontinued due to adverse events for either mirtazapine or paroxetine.

Effect of apoE Genotype on Efficacy of Treatment

Baseline scores (Day 0)

Baseline scores for HDRS-21, HDRS-17, GDS, and CGI did not differ between treatment groups. Likewise, baseline scores for $\epsilon 4$ carriers and non-$\epsilon 4$ carriers in the paroxetine and the mirtazapine treated groups were not significantly different.

Day 7

At day 7 of treatment there was a significantly greater improvement in HDRS-17 scores among mirtazapine-treated patients than among paroxetine-treated patients. Across both treatment groups, there was no significant difference in mean HDRS-17 and HDRS-21 scores between $\epsilon 4$ carriers and non-$\epsilon 4$ carriers. Also, at day 7 there were no significant differences in the number of HDRS-17 50% responders, HDRS-21 50% responders, HDRS-17 remitters, or GDS 50% responders.

Day 14

Significantly greater improvement among mirtazapine-treated patients than among paroxetine-treated patients was seen at day 14 of treatment for HDRS-17 HDRS-21, and CGI scores. Also, at day 14 there was a significant interaction between treatment group and apoE genotype effects on HDRS-17 ($p=0.036$), HDRS-21 ($p=0.033$), and CGI ($p=0.029$) scores, with mirtazapine subjects carrying an $\epsilon 4$ allele showing significantly lower scores, indicating greater improvement in mood, than those without an $\epsilon 4$ allele. Conversely, among paroxetine treated patients, those with an $\epsilon 4$ allele showed higher scores on the HDRS-17, HDRS-21, and CGI than did those without an $\epsilon 4$ allele.

Also at day 14 of treatment, GDS scores were significantly lower among $\epsilon 4$ carriers than among non-$\epsilon 4$ carriers across both treatment groups ($p=0.025$). However, this difference was primarily due to a large decrease in GDS scores among mirtazapine treated patients with an $\epsilon 4$ allele (p=0.021), whereas there was no significant difference in GDS scores among mirtazapine-treated subjects without an ε4 allele and paroxetine-treated subjects with and without an ε4 allele at day 14.

Further, at day 14 there were significantly more HDRS 17 50% responders among mirtazapine treated patients with an ε4 allele than among those without an ε4 allele (p=0.049). By contrast, at day 14 none of the paroxetine treated patients with an ε4 allele showed a 50% decrease in HDRS-17 score over baseline; all paroxetine treated patients meeting this criterion were among those without an ε4 allele. Similarly, there were significantly more HDRS-17 remitters among ε4 carriers in the mirtazapine treated group (28%) than among those without an ε4 allele (7.1 %) (p=0.005). Among paroxetine treated patients, none of those with an ε4 allele met this criterion for improvement. Mirtazapine treated patients carrying an ε4 allele showed a trend toward a greater number of HDRS-21 50% responders (48%) than did those without an ε4 allele (29.4%) (p=0.085). However, among paroxetine treated subjects, none of those carrying an ε4 allele met this criterion at day 14, whereas among those without an ε4 allele 23.3% were HDRS-21 50% responders (p=0.01). Mirtazapine treated patients with an ε4 allele were significantly more likely to show a 50% reduction in GDS score at day 14 than were those without an ε4 allele (p=0.046), whereas among paroxetine treated patients there was no difference in the number of responders between apoE genotype groups.

Day 28

A similar effect was seen at day 28 when significantly more mirtazapine treated patients with an ε4 allele showed a 50% reduction in GDS score than did noncarriers (p<0.005), but among paroxetine treated patients there was no effect of apoE genotype.

Effect of apoE Genotype on Measures of Cognition

We also examined the effect of apoE genotype on measures of cognition among mirtazapine and paroxetine treated patients. At week 8, analysis of covariance showed that mean MMSE score was significantly lower among paroxetine treated patients carrying an ε4 allele than among noncarriers (p=0.018). For mirtazapine treated patients, apoE genotype had no effect on mean MMSE at week 8.

Analysis of Caucasian Patients

Comparison of treatment groups for ethnicity showed that there were no differences in the number of non-Caucasian patients with and without the ε4 allele for mirtazapine treated subjects. For paroxetine treated patients, there were significantly more non-Caucasians among subjects with an ε4 allele (p=0.016). Because the effects of the apoE ε4 allele can depend on genetic background (Farrer, L. A. et al., JAMA 278:1349–1356, 1997), we re-analyzed our data with only Caucasian subjects, There were not enough non-Caucasian subjects in the study cohort (20 out of 246) to analyze data for these subjects separately for genotype by treatment interactions.

Among Caucasian subjects, there were no differences in final daily dosage achieved, dosing compliance, or plasma drug concentrations between ε4 carriers and non-ε4 carriers for either mirtazapine or paroxetine. There were no significant differences between ε4 carriers and noncarriers in the number of patients who discontinued due to adverse events for either mirtazapine or paroxetine. The mean age and the frequencies of males and females did not differ between ε4 carriers and noncarriers for either mirtazapine or paroxetine treated Caucasian patients.

The same interaction between apoE genotype and medication on treatment outcome were observed among Caucasian patients as in the full cohort. At baseline there were no differences between ε4 carriers and noncarriers for any of the measures of mood at baseline. At day 14, mean scores for the HDRS-17 and the HDRS-21 were significantly lower for mirtazapine than for paroxetine (p=0.006). There was a significant interaction between apoE genotype and medication for HDRS-17 score (p=0.036) and HDRS-21 score (p=0.033). Mirtazapine subjects with an ε4 allele showed greater improvement than those without an ε4 allele, whereas among paroxetine treated patients, HDRS scores for ε4 carriers showed lees improvement than did those of noncarriers. Day 14 GDS scores were significantly lower for ε4 carriers than for noncarriers treated with mirtazapine (p=0.025), but apoE genotype had no effect on GDS scores among paroxetine treated subjects. For the CGI, day 14 scores were significantly better for mirtazapine treated subjects than for paroxetine treated subjects (p=0.037). Among mirtazapine treated Caucasian patients, CGI scores were significantly better for ε4 carriers than for noncarriers (p=0.028), but for paroxetine treated patients there were no differences between ε4 carriers and noncarriers.

Significant interactions between medication and apoE genotype at day 14 were also observed in Caucasian subjects in criteria for treatment response including 50% reduction in HDRS-17 (p=0.036) and HDRS-21 (p=0.007), HDRS-17 remission (p=0.023), and 50% reduction in GDS (0.042). For each measure the percentage of ε4 carriers responding to medication treatment was greater for mirtazapine than for paroxetine. Similarly, at day 28 for mirtazapine there were significantly more patients showing a 50% reduction in GDS score (41.7%) among ε4 carriers than among noncarriers (16.9%) (p=0.012), whereas among paroxetine-treated subjects there was no significant effect of the ε4 genotype on the number of patients showing a 50% reduction in GDS. On measures of cognition, there was a trend for paroxetine treated Caucasian subjects with an ε4 allele to show a lower MMSE score than those without an ε4 allele (p=0.05). No other medication by genotype interactions were observed for cognitive measures.

As the results set forth in the above example demonstrate, mirtazapine showed a higher rate of antidepressant response in the early weeks of treatment than paroxetine. Among mirtazapine-treated subjects, this early response was significantly stronger among ε4 carriers than among non-ε4 carriers. Paroxetine showed a slower onset of anti-depressant action, with ε4 carriers being particularly slow to respond to this medication. Consequently, based on these results, improved therapeutic response for major depression can be achieved by determining the apolipoprotein E genotype of a human patient and administering mirtazapine to those patients who are carrying the apoE4 gene.

What is claimed is:

1. A method for improving the therapeutic response to mirtazapine in a human patient with major depression comprising administering mirtazapine, in an amount effective to treat major depression, to said patient, wherein said patient has been determined to be a carrier of the gene for apolipoprotein E4.

2. A method according to claim 1, wherein said patient has been determined to be a carrier of said gene by nucleic acid sequencing of DNA.

3. A method according to claim 2, wherein said nucleic acid sequencing comprises restriction isotyping.

4. A method according to claim 1, wherein said patient has been determined to be a carrier of said gene by examining said patient to determine which apolipoprotein isoforms are present in the patient's plasma.

5. A method comprising:
   determining the apolipoprotein E genotype of a human patient; and
   administering mirtazapine, in an amount effective to treat major depression, to a patient with major depression who is found to carry the gene for Apolipoprotein E4.

6. A method according to claim 5, wherein determining the apolipoprotein E genotype comprises screening patients to determine the type and number of apolipoprotein E alleles present in a patient.

7. A method according to claim 6, wherein said screening may be carried out by nucleic acid sequencing of DNA.

8. A method according to claim 7, wherein said nucleic acid sequencing comprises restriction isotyping.

9. A method according to claim 6, wherein said screening comprises examining a patient to determine which apolipoprotein isoforms are present in the patient's plasma.

10. A method according to claim 5, wherein said mirtazapine is administered in an amount ranging from 15 to 45 mg per day.

11. A method according to claim 6, wherein said mirtazapine is administered in an amount ranging from 15 to 45 mg per day.

12. A method according to claim 7, wherein said mirtazapine is administered in an amount ranging from 15 to 45 mg per day.

13. A method according to claim 8, wherein said mirtazapine is administered in an amount ranging from 15 to 45 mg per day.

14. A method according to claim 9, wherein said mirtazapine is administered in an amount ranging from 15 to 45 mg per day.

15. A method according to claim 2, wherein said mirtazapine is administered in an amount ranging from 15 to 45 mg per day.

16. A method according to claim 3, wherein said mirtazapine is administered in an amount ranging from 15 to 45 mg per day.

17. A method according to claim 4, wherein said mirtazapine is administered in an amount ranging from 15 to 45 mg per day.

18. A method according to claim 1, wherein said mirtazapine is administered in an amount ranging from 15 to 45 mg per day.

\* \* \* \* \*